United States Patent [19]

Siri

[11] Patent Number: Plant 6,123

[45] Date of Patent: Mar. 8, 1988

[54] MINIATURE CARNATION SANDY

[75] Inventor: Angelo J. Siri, San Francisco, Calif.

[73] Assignee: Siri Bros. Nursery Inc., East Palo Alto, Calif.

[21] Appl. No.: 641,921

[22] Filed: Aug. 17, 1984

[51] Int. Cl.[4] ..... A01H 5/00

[52] U.S. Cl. ..... Plt./71

[58] Field of Search ..... Plt./70–71

*Primary Examiner*—Robert E. Bagwill

*Attorney, Agent, or Firm*—Limbach, Limbach & Sutton

[57] ABSTRACT

A miniature carnation plant having lavender blossoms.

1 Drawing Sheet

BACKGROUND OF THE NEW PLANT

This invention comprises a new and distinct miniature carnation variety that has its own set of characteristics that set it apeart from all other varieties of miniature carnations. The newly discovered variety, called "Sandy," originated as a sport of Lilac, an unpatented variety.

The botantical classification of the new variety is *Dianthus caryophyllus longicaulis*. The commercial classification is Miniature Carnation. The plant takes the form of a bush.

Asexual propogation of the newly discovered miniature carnation variety has been made at Siri Brothers Nursery, Inc. at East Palo Alto, Calif., by taking cuttings. The cuttings so taken and grown have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

FIG. 2, shows the proper color of the new variety although in that figure, the illustrated color of the prior art Lilac is slightly faded.

FIG. 1 is not as representative of the colors of the new variety as FIG. 2.

DESCRIPTION OF THE NEW PLANT

Figure 1:
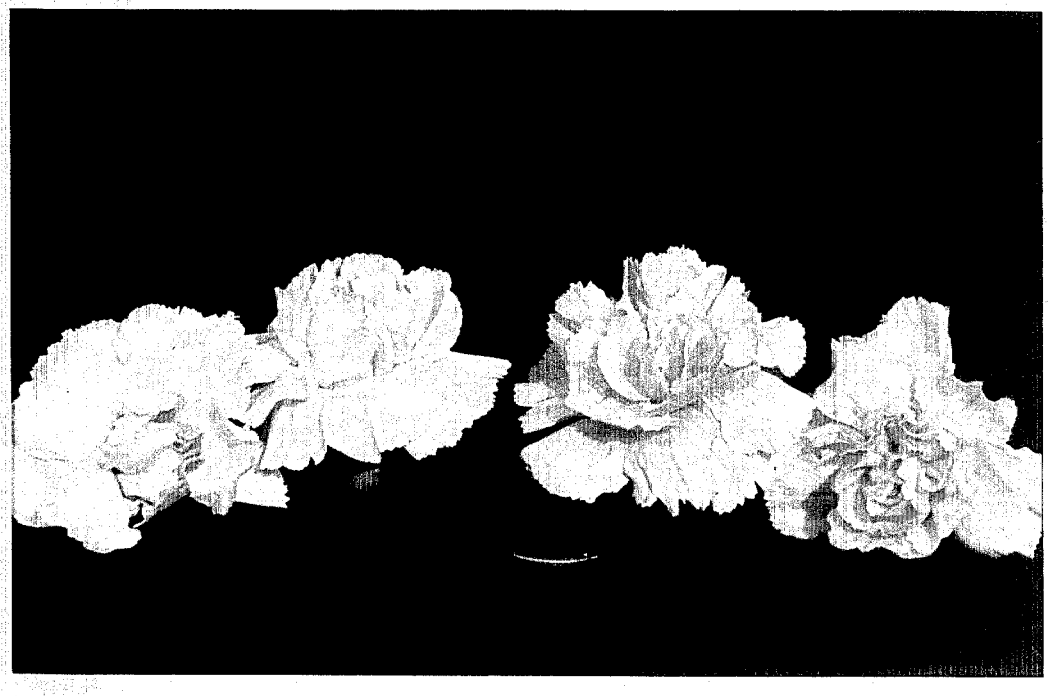
FIG. 1. PRIOR ART
FIG. 1 is an enlarged view of the bloom of the new variety Sandy on the right and showing the parent Lilac on the left.
Figure 2:
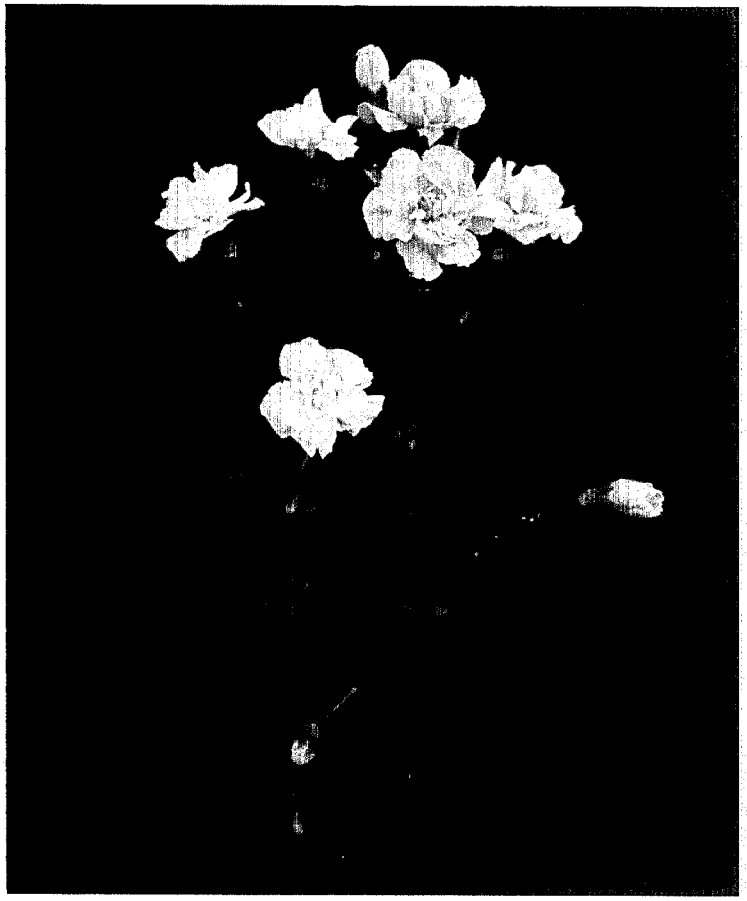
FIG. 2 is a view of the sprays of the new variety Sandy on the right and the prior art Lilac on the left.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "RHS" for The Royal Horticultural Colour Chart, Royal Horticultural Society, London, England.

GROWTH HABITS

Height: As compared to other varieties short to medium.

Foliage: Average to slightly less than average.

Speed of growth: Fast.

Root system: Average.

FOLIAGE

Leaf size:

*Length.*—At the midpoint of the stem it averages 4".

*Width.*—At the midpoint of the stem it averages ⅜".

*Features.*—N/A.

Leaf shape: Average curl with a long accuminating tip.

Leaf texture: Smooth and leathery.

Leaf color:

*Upperside.*—RHS Green Group 139A with a whitish haze over the green.

*Underside.*—RHS Green Group 139A with a whitish haze over the green.

Leaf ribs: One rib down the center from the base to the tip of the leaf.

Leaf habit: Average amount of curl.

Leaf density: Average.

STEM

Stem strength: Average.

Stem color: RHS Green Group 139A with a whitish haze over the green.

Nodes: Average.

*Space between nodes.*—3" average at midstem.

Stem branching: Very good better than average.

BUDS

Bud shape: Oval.

Bud color: The top half is LCC H-21 L-13, the bottom half is LCC H-22 L-9.

Average number of flowering buds per stem: 4–5.

Uniformity of bud opening: Very uniform.

Bud splitting: Very seldom.

Number of sepals per calyx: 5–6 mostly 5.

FLOWER

Description of the color of the bloom: It is a medium lavender color. The color is LCC H-43 L-4. During the summer months, a pale fringe appears at the edge of the petals.

General tonality of the color: Medium to bright.

Diameter of average bloom: 2½".

Bloom shape: Generally round with a high center and flat outer petals.
Keeping quality: Average.
Fragrance: Slight.

PETALAGE

Petal texture: Soft and velvety.
Petal edge: Medium seration.
Color stability: Very stable.
Petal size:
*Average length.*—1⅞".
*Average width at widest point.*—1".
Calyx color: The top half is LCC H-21 L-13, the bottom half blends into LCC H-22 L-9, the tips of the leaves on the bottom of the calyx are LCC H-22 L-15.

REPRODUCTIVE ORGANS

Stamen: With anthers.
Average length of stamen: 1".
Color of anthers: LCC H-48 L-3 with specks of LCC H-44 L-6 on them.
Color of filament: LCC H-21 L-1.
Pistils:
*Shape.*—There are usually 2 styles, sometimes 1 or 3 and sometimes none.
*Number.*—The number of pistils seems to vary considerably.
*Length from tip to ovary.*—Average of ⅞".
Stigma:
*Shape.*—Round located at the very tip of the style.

*Color.*—White.
Style:
*Color.*—It is LCC H-25 L-1 with the color LCC H-43 L-14 running from the tip to approximately 40% of the way down toward the base.
Ovary:
*Shape.*—Ovid.
*Color.*—The tip is LCC H-26 L-9, the middle is LCC H-23 L-10, the bottom is LCC H-23 L-1.
*Length.*—Approximately ⅜".
*Width.*—Approximately ⅜".

DISTINGUISHING CHARACTERISTICS BETWEEN THE NEW VARIETY AND PARENT

The distinguishing characteristic is the color of the bloom. The parent is a light lavender color while the sport is a medium lavender color that is several shades darker.

SIMILAR CHARACTERISTICS OF THE NEW VARIETY AND PARENT

All of the characteristics of both varieties are similar except for the distinguishing characteristics referred to above.

Years of asexual reproduction 1981, 1982, 1983.

I claim:

1. A new and distinct variety of miniature carnation plant, substantially as herein shown and described.

* * * * *

PRIOR ART